United States Patent [19]

Maeda et al.

[11] Patent Number: 5,760,280

[45] Date of Patent: Jun. 2, 1998

[54] PRODUCTION PROCESS FOR AROMATIC COMPOUNDS

[75] Inventors: Isamu Maeda, Misima-gun; Hiroshi Sugizawa; Noboru Saito, both of Takatsuki, all of Japan

[73] Assignee: Nippon Shokubai Co., Ltd., Japan

[21] Appl. No.: 857,356

[22] Filed: May 16, 1997

[30] Foreign Application Priority Data

May 21, 1996 [JP] Japan .................................. 8-125540

[51] Int. Cl.$^6$ .................................................. C07C 255/00
[52] U.S. Cl. .......................................... 558/425; 558/425
[58] Field of Search ............................................... 558/425

[56] References Cited

U.S. PATENT DOCUMENTS 5,565,612  10/1996  Pfirmann et al. ...................... 556/425

FOREIGN PATENT DOCUMENTS 2 122 190  1/1984  United Kingdom .

OTHER PUBLICATIONS

Nizeki et al., "Decarboxylation of Halogen–substituted Benzenecarboxylic Acid," Patent Abstracts of Japan, Publication Date Jan. 27, 1989, Publication No. 01025737, Applicant Nippon Carbide Ind Co Inc, vol. 013, No. 205 (C–595), abstract published May 15, 1989.

Roedig et al., "Aromatisierende nucleophile Substitutionen mit aliphatischen Amine und Ammoniak," Chemische Berichte, 1974, pp. 920–928, vol. 107, XP002036655, Weinheim, Germany.

Toland et al., "Exhange of mitrile and carboxyl groups in aromatic compounds," Journal of Organic Chemistry, 1958, pp. 1350–1351, vol. 23, XP002036656, Easton, USA.

*Primary Examiner*—Johann Richter
*Assistant Examiner*—Joseph Morray

[57] ABSTRACT

A process for producing aromatic compounds comprises the step of carrying out a reaction between an aromatic carboxylic acid and a polyfluorobenzonitrile, thus forming an aromatic nitrile and a polyfluorobenzene. This process can produce the aromatic compounds with few problems with respect to worker safety and at a low cost when compared with conventional processes, and can convert the starting materials for the reaction into useful substances with ease and little waste and in a high yield.

12 Claims, No Drawings

PRODUCTION PROCESS FOR AROMATIC COMPOUNDS

BACKGROUND OF THE INVENTION

A. TECHNICAL FIELD

The present invention relates to a process for producing aromatic compounds.

B. BACKGROUND ART

As to production processes for aromatic compounds such as aromatic nitriles, there are, for example, known the following processes: 1) a process utilizing a Sandmeyer reaction via a diazonium salt from an aniline compound that is an aromatic primary amine; and 2) a process in which a benzamide compound that is an aromatic primary amide is chemically dehydrated in the presence of phosphorus pentaoxide, acetic anhydride, or the like. Specifically, 2,3,4,5-tetrachloroaniline is, for example, used as the aniline compound that is a starting material in process 1) above (*J. Prakt. Chem.*, 56, 48–66 (1897)), and 2,3,4,5-tetrachlorobenzamide is, for example, used as the amide compound that is a starting material in process 2) above (*Chem. Ber.*, 107, 920–923 (1974)). In these processes, 2,3,4,5-tetrachlorobenzonitrile is obtained as the aromatic nitrile.

However, as to the above-mentioned conventional production processes for aromatic nitriles, because the aniline compound and the benzamide compound themselves, which are used as starting materials, are generally expensive and often difficult to obtain, the production cost tends to be so high that there are difficulties in practical or economical use. In addition, because a stoichiometric amount of highly toxic inorganic cyanide compound or chemical dehydrator needs to be used, there are also problems with respect to worker safety.

SUMMARY OF THE INVENTION

A. OBJECTS OF THE INVENTION

It is an object of the present invention to provide a process which can produce an aromatic nitrile with few problems with respect to worker safety and at a low cost.

In addition, it is another object of the present invention to provide a production process for aromatic compounds, which process can convert starting materials for reaction into useful substances with ease so as to produce a high yield and involve little waste.

B. DISCLOSURE OF THE INVENTION

The present inventors worked diligently to solve the above-mentioned problems and encountered some surprising solutions. As a result, they attained the present invention by finding that if an aromatic carboxylic acid, which has low toxicity and is industrially easily available and inexpensive, and a specific polyfluorobenzonitrile are used as starting materials for reaction and reacted with each other, a series of unexpected specific reactions including mutual addition, exchange, and decarboxylation between a carboxyl group of the aromatic carboxylic acid and a nitrile group of the polyfluorobenzonitrile occur to produce an aromatic nitrile, which is an aromatic compound, and a polyfluorobenzene, which is also an aromatic compound, at a low cost, with ease, and with high yield.

Thus, a process for producing aromatic compounds, according to the present invention, comprises the step of carrying out a reaction between an aromatic carboxylic acid and a polyfluorobenzonitrile, thus forming an aromatic nitrile and a polyfluorobenzene.

The process of the present invention may further comprise the step of isolating the formed aromatic nitrile after the reaction between the aromatic carboxylic acid and the polyfluorobenzonitrile.

The process of the present invention may further comprise the step of isolating the formed polyfluorobenzene after the reaction between the aromatic carboxylic acid and the polyfluorobenzonitrile.

In the process of the present invention, the reaction may be carried out at a temperature of between about 180° and about 300° C.

In the process of the present invention, the reaction may be carried out while carbon dioxide or both of carbon dioxide and the polyfluorobenzene which form during the reaction are discharged from a reaction system.

The process of the present invention may further comprise the step in which a reaction intermediate that is an adduct from a carboxyl group and a nitrile group, including an adduct from the aromatic carboxylic acid and the polyfluorobenzonitrile and forming in the course of the reaction therebetween, is re-used for a new reaction between an aromatic carboxylic acid and a polyfluorobenzonitrile.

In the process of the present invention, the aromatic carboxylic acid may be 2,3,4,5-tetrachlorobenzoic acid.

In the process of the present invention the polyfluorobenzonitrile may be pentafluorobenzonitrile.

These and other objects and advantages of the present invention will be more fully apparent from the following detailed disclosure.

DETAILED DESCRIPTION OF THE INVENTION

Although not especially limited, examples of the aromatic carboxylic acid, which is used as a reactant, are benzoic acid, terephthalic acid, isophthalic acid, naphthalenemonocarboxylic acid, naphthalenedicarboxylic acid, and nuclear-substituted matters thereof (e.g. methyl-, methoxy-, phenoxy-, chloro-, bromo-, iodo-, and nitro-substituted ones). Of these compounds, chloro-substituted benzoic acids, particularly 2,3,4,5-tetrachlorobenzoic acid, are especially preferably used, because they can give 2,3,4,5-tetrachlorobenzonitrile that is an aromatic nitrile that is especially important as a starting material for medicines.

Although not especially limited, examples of the polyfluorobenzonitrile, which is used as a reactant, are difluorobenzonitrile, trifluorobenzonitrile, tetrafluorobenzonitrile, nuclear-substituted matters thereof (e.g. chloro-, bromo-, iodo-, and nitro-substituted ones), and pentafluorobenzonitrile. Of these compounds, pentafluorobenzonitrile is particularly preferably used because, as mentioned below, it can provide pentafluorobenzene that is a polyfluorobenzene that is especially important as a starting material for polymerization catalysts.

Although not especially limited, the ratio of the polyfluorobenzonitrile to the aromatic carboxylic acid is, for example, preferably in a range of about 0.1 to about 10 equivalents, more preferably about 0.5 to about 8 equivalents, and even more preferably about 2 to about 5 equivalents. In practical use, such preferred ranges provide advantages such as enhancing apparatus efficiency.

The manner of carrying out the reaction between the aromatic carboxylic acid and the polyfluorobenzonitrile is not especially limited and may be either a batch process or a continuous process. However, a batch process is preferable with respect to practical use, for example, in view of the conversion of the reactants.

Although not especially limited, examples of the reaction vessel are pressure-resistant reaction vessels such as autoclaves. Of the reaction vessels, constant-pressure reaction vessels are preferable with respect to practical use.

The reaction between the aromatic carboxylic acid and the polyfluorobenzonitrile is preferably carried out under catalyst-free conditions for economical advantages or to save labor costs for separation purification operations after the completion of the reaction. However, as needed, the reaction may be carried out in the presence of an acid catalyst to promote the reaction. Although not especially limited, examples of the acid catalyst are as follows: inorganic acids such as phosphoric acid and boric acid; solid acids such as acid clay and acid alumina. Of these catalysts, the solid acids are preferable with respect to practical use, for example in view of separation purification. The acid catalyst may be used alone or in adequate combinations of two or more thereof.

When the acid catalyst is used, the amount thereof is not especially limited, but the amount is, for example, preferably in a range of about 0.1 to about 10 mol %, more preferably about 0.5 to about 5 mol %, and even more preferably about 1 to about 3 mol % of the aromatic carboxylic acid with one purpose behind such preferred ranges being to conserve the amount of acid catalyst used and therefore conserve resources.

Because the polyfluorobenzonitrile can also serve as a solvent, it is preferable to carry out the reaction between the aromatic carboxylic acid and the polyfluorobenzonitrile with no solvent other than the polyfluorobenzonitrile to, for example, save labor for separation purification operations after the completion of the reaction. However, if need arises, the reaction may be carried out using solvents inert to the reaction, such as aromatic hydrocarbons (e.g. xylene, pseudocumene, durene), high boiling point solvents (e.g. nitrotoluene, benzyltoluene), alone or in adequate combinations of two or more thereof.

When a solvent other than the polyfluorobenzonitrile is used, the amount of this solvent is not especially limited, but the amount is, for example, preferably in a range of about 10 to about 1,000% by weight, more preferably about 30 to about 500% by weight, and even more preferably about 50 to about 200% by weight, of the aromatic carboxylic acid. Such preferred ranges provide advantages in practical use such as enhancing apparatus efficiency.

The reaction temperature is, for example, preferably in a range of about 180° to about 300° C., more preferably about 200° to about 280° C., and even more preferably about 220° to about 260° C. Such preferred ranges provide advantages such as the inhibition of side reactions and a more preferred rate of reaction.

The reaction duration depends on various factors, for example, the reaction temperature, the presence or absence of the catalyst, the type and amount of the catalyst, the type and composition of the starting materials for the reaction, and therefore is not especially limited, but the reaction duration is, for example, preferably in a range of about 0.5 to about 50 hours, more preferably about 1 to about 30 hours, and even more preferably about 2 to about 20 hours. In practical use, such preferred ranges provide advantages such as providing a more efficient conversion of the reactants and a higher yield.

If the aromatic carboxylic acid and the polyfluorobenzonitrile are reacted with each other, a mutual addition-exchange reaction between a carboxyl group of the aromatic carboxylic acid and a nitrile group of the polyfluorobenzonitrile occurs as an equilibrium reaction to give an aromatic nitrile. A polyfluorobenzoic acid is also expected to form in this reaction, but the resultant polyfluorobenzoic acid is unexpectedly easily subjected to irreversible decarboxylation during the above-mentioned reaction and thereby rapidly converted into a polyfluorobenzene. Therefore, the present inventors infer that the aromatic nitrile, the polyfluorobenzene, and a reaction intermediate, which is an adduct from a carboxyl group of the aromatic carboxylic acid or polyfluorobenzoic acid and a nitrile group of the polyfluorobenzonitrile or aromatic nitrile, are included as reaction products in a reaction mixture as obtained by the reaction between the aromatic carboxylic acid and the polyfluorobenzonitrile, and that the polyfluorobenzoic acid does not coexist in the reaction mixture.

Thus, in the process of the present invention, the aromatic nitrile and the polyfluorobenzene are efficiently produced from the irreversible reaction involving the decarboxylation. Because the polyfluorobenzene is also very useful in industries, it can be utilized for various purposes by being recovered from the reaction mixture. Thus, the process of the present invention can convert the starting materials for the reaction into useful substances with ease and in a high yield, and with little waste.

As mentioned above, the decarboxylation occurs in the course of the reaction between the aromatic carboxylic acid and the polyfluorobenzonitrile, thereby giving carbon dioxide and the aforementioned polyfluorobenzene with a boiling point of about 80° to about 90° C. under normal pressure (e.g. pentafluorobenzene has a boiling point of about 85° C. under normal pressure). Therefore, in the case where a reaction vessel that is closed up tight is used, the reaction pressure increases with the progress of the reaction. The level of the reaction pressure in such a case, depending on the reaction temperature and the space volume ratio of the reaction vessel may reach about 50 kg/cm$^2$ for example, within the aforementioned reaction temperature range. Therefore, considering the pressure resistance of the reaction vessel, it is preferable that the reaction is carried out while carbon dioxide or both of carbon dioxide and the polyfluorobenzene which form during the reaction are discharged from a reaction system. If the reaction is carried out in such a way, the reaction pressure can be suppressed, for examples, to not higher than about 10 kg/cm$^2$.

For the purpose of increasing the product yield even more, the production process of the present invention may further comprise the step in which a reaction intermediate that is an adduct from a carboxyl group and a nitrile group, including an adduct from the aromatic carboxylic acid and the polyfluorobenzonitrile and forming in the course of the reaction therebetween, is re-used for a new reaction between an aromatic carboxylic acid and a polyfluorobenzonitrile. Such a re-using step can increase the product yield and therefore is very advantageous in industrial practical use.

The aromatic nitrile and the polyfluorobenzene, formed by the reaction between the aromatic carboxylic acid and the polyfluorobenzonitrile, can be easily separated and purified by conventional methods, for example, distillation, extraction, crystallization, after the reaction has finished.

Advantages of the invention include the following:

In the production process of the present invention, because an aromatic carboxylic acid and a polyfluorobenzonitrile were reacted with each other, an aromatic nitrile and a polyfluorobenzene can be produced with ease and with high yield. Because the aromatic carboxylic acid, which is used as one of the starting materials for the reaction, has low toxicity, and because the other starting material for the reaction, namely, polyfluorobenzonitrile, also has relatively low toxicity, worker safety is enhanced. The above-mentioned starting materials for the reaction are both easy to industrially obtain, so the aromatic nitrile and the polyfluorobenzene can be produced practically and at a low cost.

The resultant aromatic nitrile is useful as a starting material for organic synthesis, and polychlorobenzonitriles, particularly 2,3,4,5-tetrachlorobenzonitrile, are especially important as starting materials for medicines and agricultural chemicals.

In the present invention, the polyfluorobenzene as well as the aromatic nitrile is obtained. The polyfluorobenzene is useful as a starting material for organic synthesis and pentafluorobenzene is particularly important as a starting material for polymerization catalysts. Accordingly, the present invention process can convert the starting materials for the reaction into useful substances with ease and in a high yield, and with little waste.

DETAILED DESCRIPTION OF THE PREFERRED EMBODIMENTS

Hereinafter, the present invention is more specifically illustrated by the following examples of some preferred embodiments (which relate to the invention) in comparison with comparative examples (which do not relate to the invention). However, the present invention is not limited to the below-mentioned examples of the preferred embodiments.

EXAMPLE 1

First, 4.5 g (17.3 mmol) of 2,3,4,5-tetrachlorobenzoic acid and 13.4 g (69.4 mmol) of pentafluorobenzonitrile were placed into a small-sized autoclave of 100 ml in capacity made of Hastelloy C and equipped with a stirrer. The inner atmosphere of the autoclave was replaced with a nitrogen gas of atmospheric pressure, and then the autoclave was heated at 230° C. for 6 hours in a closed-up state, whereby the reaction pressure gradually increased up to 9.5 kg/cm$^2$ with time. However, after the completion of the reaction, the pressure fell to 2.5 kg/cm$^2$ at 20° C. Thus, a reaction mixture was obtained in a yield of 17.3 g.

The reaction mixture was analyzed by $^1$H-NMR and $^{19}$F-NMR. As a result, the conversion was 98% based on the original molar number of 2,3,4,5-tetrachlorobenzoic acid. In addition, 2,3,4,5-tetrachlorobenzonitrile and pentafluorobenzene were formed in yields of 86% and 74% respectively, and the rest of the products were reaction intermediates, and no pentafluorobenzoic acid was detected.

Next, 17.0 g of the reaction mixture was distilled under normal pressure to obtain pentafluorobenzene in a yield of 2.0 g as a fraction having a boiling point of 80° to 90° C. Subsequently, the residual liquid was subjected to crystallization filtration at 5° C. to obtain 2,3,4,5-tetrachlorobenzonitrile in a yield of 3.2 g in terms of solid content.

Furthermore, the filtrate was distilled under a reduced pressure of 20 mmHg to obtain pentafluorobenzonitrile in a yield of 10.0 g as a fraction having a boiling point of 50° to 60° C., and the amount of the balance was 1.8 g.

The analysis showed that the purity of each product was 95% and the recovery was 92%, and that the balance was mainly an adduct that was a reaction intermediate.

EXAMPLE 2

The reaction was carried out in the same way as of Example 1 except that 1.5 g of the adduct, which was a reaction intermediate as obtained in Example 1, was added.

As a result, the reaction pressure reached 11.5 kg/cm$^2$ during the reaction and fell to 3.0 kg/cm$^2$ after the completion of the reaction, and the conversion was 98%. In addition, the yields of 2,3,4,5-tetrachlorobenzonitrile and pentafluorobenzene were 92% and 90% respectively, and no pentafluorobenzoic acid was detected.

Thus, the re-using of the reaction intermediate greatly increased the yields of the objectives.

EXAMPLE 3

The reaction was carried out in the same way as Example 1 except that the reaction temperature was changed to 200° C.

As a result, the reaction pressure reached 3.5 kg/cm$^2$ during the reaction and fell to 1.0 kg/cm$^2$ at 20° C. after the completion of the reaction, and the conversion was 77%. In addition, the yields of 2,3,4,5-tetrachlorobenzonitrile and pentafluorobenzene were 33% and 20% respectively, and no pentafluorobenzoic acid was detected.

EXAMPLE 4

The reaction was carried out in the same way as of Example 1 except that the amount of 2,3,4,5-tetrachlorobenzoic acid was changed to 9.0 g (34.6 mmol).

As a result, the reaction pressure reached 13.5 kg/cm$^2$ during the reaction and fell to 4.5 kg/cm$^2$ at 20° C. after the completion of the reaction, and the conversion was 98%. In addition, the yields of 2,3,4,5-tetrachlorobenzonitrile and pentafluorobenzene were 84% and 65% respectively, and no pentafluorobenzoic acid was detected.

EXAMPLE 5

The reaction was carried out in the same way as of Example 1 except that the amount of 2,3,4,5-tetrachlorobenzoic acid was replaced with 2.7 g (17.3 mmol) of p-chlorobenzoic acid.

As a result, the reaction pressure was almost the same as that in Example 1, and the conversion was 96%. In addition, the yields of p-chlorobenzonitrile and pentafluorobenzene were 71% and 61% respectively, and no pentafluorobenzoic acid was detected.

EXAMPLE 6

The reaction was carried out in the same way as of Example 4 except that the reaction pressure was regulated to 8 kg/cm$^2$ with a constant-pressure apparatus.

As a result, carbon dioxide was discharged from the constant-pressure apparatus during the reaction; and the pressure fell to 2.0 kg/cm$^2$ at 20° C. after the completion of the reaction, and the conversion was 98%. In addition, the yields of 2,3,4,5-tetrachlorobenzonitrile and pentafluorobenzene were 85% and 70% respectively, and no pentafluorobenzoic acid was detected.

EXAMPLE 7

The reaction was carried out in the same way as of Example 3 except that the reaction duration was changed to 30 hours.

As a result, the reaction pressure reached 9.0 kg/cm$^2$ during the reaction and fell to 2.5 kg/cm$^2$ at 20° C. after completion of the reaction, and the conversion was 97%. In addition, the yields of 2,3,4,5-tetrachlorobenzonitrile and pentafluorobenzene were 86% and 76% respectively, and no pentafluorobenzoic acid was detected.

COMPARATIVE EXAMPLE 1

The reaction was carried out in the same way as of Example 1 except that the reaction temperature was changed to 165° C.

As a result, the reaction pressure was atmospheric, and the conversion was 33%. However, none of carbon dioxide, 2,3,4,5-tetrachlorobenzonitrile, and pentafluorobenzene was formed, and only a reaction intermediate was formed, and no pentafluorobenzoic acid was detected.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

What is claimed is:

1. A process for producing aromatic compounds, which comprises the step of carrying out a reaction between an aromatic carboxylic acid and a polyfluorobenzonitrile, thus forming an aromatic nitrile and a polyfluorobenzene.

2. A process according to claim 1, further comprising the step of isolating the formed aromatic nitrile after the reaction between the aromatic carboxylic acid and the polyfluorobenzonitrile.

3. A process according to claim 1, further comprising the step of isolating the formed polyfluorobenzene after the reaction between the aromatic carboxylic acid and the polyfluorobenzonitrile.

4. A process according to claim 1, wherein the reaction is carried out at a temperature of between about 180° and about 300° C.

5. A process according to claim 1, wherein the reaction is carried out while carbon dioxide or both of carbon dioxide and the polyfluorobenzene which form during the reaction are discharged from a reaction system.

6. A process according to claim 1, further comprising the step in which a reaction intermediate that is an adduct from a carboxyl group and a nitrile group, including an adduct from the aromatic carboxylic acid and the polyfluorobenzonitrile and forming in the course of the reaction therebetween, is re-used for a new reaction between an aromatic carboxylic acid and a polyfluorobenzonitrile.

7. A process according to claim 1, wherein the aromatic carboxylic acid is 2,3,4,5-tetrachlorobenzoic acid.

8. A process according to claim 1, wherein the polyfluorobenzonitrile is pentafluorobenzonitrile.

9. A process of claim 1 wherein polyfluorobenzoic acid production is minimized.

10. A process of claim 1 wherein polyfluorobenzoic acid production is effectively absent.

11. A process for producing aromatic compounds, which comprises the step of carrying out a reaction between 2,3,4,5-tetrachlorobenzoic acid and pentafluorobenzonitrile, thus forming 2,3,4,5-tetrachlorobenzonitrile and pentafluorobenzene.

12. A solvent-free, catalytic-free and batch process for producing aromatic compounds, which comprises the step of carrying out an effectively solvent-free and effectively catalytic-free batch reaction in a closed vessel between an aromatic carboxylic acid and a polyfluorobenzonitrile wherein carbon dioxide or both of carbon dioxide and a polyfluorobenzene are discharged from the closed vessel during at least a portion of the reaction, thus forming an aromatic nitrile and a polyfluorobenzene.

* * * * *